US010159580B2

(12) United States Patent
Guizzardi et al.

(10) Patent No.: US 10,159,580 B2
(45) Date of Patent: Dec. 25, 2018

(54) VERTEBRAL FUSION DEVICE AND SYSTEM

(71) Applicants: TSUNAMI S.R.L., Modena (IT);
Giancarlo Guizzardi, Florence (IT);
Piero Petrini, Perugia (IT)

(72) Inventors: Giancarlo Guizzardi, Florence (IT);
Piero Petrini, Citta di Castello (IT)

(73) Assignees: TSUNAMI S.R.L., Modena (IT);
Giancarlo Guizzardi, Florence (IT);
Piero Petrini, Perugia (IT)

( * ) Notice: Subject to any disclaimer, the term of this patent is extended or adjusted under 35 U.S.C. 154(b) by 541 days.

(21) Appl. No.: 14/436,636

(22) PCT Filed: Oct. 21, 2013

(86) PCT No.: PCT/IB2013/059520
§ 371 (c)(1),
(2) Date: Apr. 17, 2015

(87) PCT Pub. No.: WO2014/061005
PCT Pub. Date: Apr. 24, 2014

(65) Prior Publication Data
US 2015/0282944 A1 Oct. 8, 2015

(30) Foreign Application Priority Data

Oct. 19, 2012 (IT) ................. PI2012A0106

(51) Int. Cl.
*A61F 2/44* (2006.01)
*A61B 17/02* (2006.01)
(Continued)

(52) U.S. Cl.
CPC .......... *A61F 2/4455* (2013.01); *A61B 17/025* (2013.01); *A61B 17/707* (2013.01);
(Continued)

(58) Field of Classification Search
None
See application file for complete search history.

(56) References Cited

U.S. PATENT DOCUMENTS 5,549,679 A * 8/1996 Kuslich .............. A61B 17/7098
606/247
6,037,519 A * 3/2000 McKay ..................... A61F 2/28
423/305
(Continued)

FOREIGN PATENT DOCUMENTS

CN 101444435 B 12/2010
DE 10253169 A1 8/2004
(Continued)

OTHER PUBLICATIONS

International Search Report dated Apr. 28, 2014, corresponding to International Patent Application No. PCT/IB2013/059520.

*Primary Examiner* — Zade Coley
(74) *Attorney, Agent, or Firm* — Ladas & Parry LLP; Malcolm J. MacDonald (57) ABSTRACT

A vertebral fusion device having a support element configured for insertion between two corresponding vertebral portions of two adjacent vertebrae, such as spinous processes and transverse processes, or joint surfaces of the vertebral bodies or of the facets, comprising a granular osteosynthesis material, preferably in cortico-spongeous chips made of bone bank human bone, which is plastically deformable, and a hollow container body that contains the osteosynthesis material and has a side wall, for example made with a network of interlaced meshes, and two open end portions to allow a contact between the osteosynthesis material and respective surfaces of said corresponding vertebral portions, so that the osteosynthesis material is kept in (Continued)

a compressed condition between said corresponding vertebral portions and receives mechanical loads therefrom which promote osteosynthesis.

20 Claims, 6 Drawing Sheets

(51) Int. Cl.
    *A61B 17/70*     (2006.01)
    *A61F 2/30*     (2006.01)

(52) U.S. Cl.
    CPC ...... *A61B 17/7064* (2013.01); *A61B 17/7065* (2013.01); *A61F 2/442* (2013.01); *A61B 2017/0256* (2013.01); *A61F 2/30965* (2013.01); *A61F 2/446* (2013.01); *A61F 2002/30736* (2013.01); *A61F 2250/0067* (2013.01); *A61F 2310/00023* (2013.01)

(56) References Cited

U.S. PATENT DOCUMENTS

| | | | | |
|---|---|---|---|---|
| 6,126,688 | A * | 10/2000 | McDonnell | A61F 2/446 623/17.16 |
| 7,041,309 | B2 * | 5/2006 | Remington | A61F 2/4455 424/423 |
| 7,048,762 | B1 * | 5/2006 | Sander | A61F 2/4644 623/17.11 |
| 7,074,239 | B1 * | 7/2006 | Cornwall | A61B 17/707 606/246 |
| 8,088,402 | B2 * | 1/2012 | Remington | A61L 27/56 424/423 |
| 2005/0055094 | A1 * | 3/2005 | Kuslich | A61F 2/442 623/17.11 |
| 2005/0119747 | A1 * | 6/2005 | Fabris Monterumici | A61B 17/025 623/17.11 |
| 2006/0142858 | A1 * | 6/2006 | Colleran | A61F 2/4465 623/17.11 |
| 2006/0233853 | A1 * | 10/2006 | Remington | A61F 2/4455 424/422 |
| 2007/0083200 | A1 * | 4/2007 | Gittings | A61B 17/7071 606/279 |
| 2007/0167947 | A1 * | 7/2007 | Gittings | A61B 17/7071 606/86 A |
| 2007/0191950 | A1 * | 8/2007 | Arnin | A61B 17/7043 623/17.11 |
| 2008/0167686 | A1 * | 7/2008 | Trieu | A61F 2/442 606/249 |
| 2008/0319487 | A1 * | 12/2008 | Fielding | A61B 17/7053 606/263 |
| 2010/0057114 | A1 * | 3/2010 | Butler | A61B 17/00234 606/151 |
| 2010/0204699 | A1 * | 8/2010 | Wei | A61F 2/30 606/76 |
| 2011/0054408 | A1 * | 3/2011 | Wei | A61B 17/68 604/175 |
| 2011/0295323 | A1 * | 12/2011 | Hudgins | A61B 17/7064 606/279 |
| 2012/0276204 | A1 * | 11/2012 | Remington | A61F 2/4455 424/484 |
| 2013/0144386 | A1 * | 6/2013 | Horton | A61F 2/4455 623/17.11 |
| 2013/0184826 | A1 * | 7/2013 | Thaiyananthan | A61F 2/442 623/17.16 |

FOREIGN PATENT DOCUMENTS

| | | | | |
|---|---|---|---|---|
| FR | | 3011458 A1 * | 4/2015 | ......... A61B 17/7062 |
| WO | | 0247587 A2 | 6/2002 | |
| WO | | 2009005819 A1 | 1/2009 | |
| WO | | 2009006258 A1 | 1/2009 | |

* cited by examiner

VERTEBRAL FUSION DEVICE AND SYSTEM

FIELD OF THE INVENTION

The present invention relates to a device and to a vertebral fusion system, i.e. to a spinal fusion device and system. A procedure is also described for implanting said device, as well as a toolkit for carrying out this procedure.

BACKGROUND OF THE INVENTION

Several devices are known for the fusion of adjacent vertebrae, among which:
instrument-assisted fusion devices, comprising rods and screws for fixing the relative position of the vertebrae;
"cage"-type fusion devices, which can be implanted by an anterior or is posterior or lateral approach;
interspinous fusion devices, suitable for positioning between the spinous processes of two adjacent vertebrae.

US2005/0055094 discloses a cage-type fusion device known as "Optimesh". This device is suitable for insertion between two vertebral bodies to replace a damaged intervertebral disc, and comprises a closed cage element that is manufactured starting from a fibrous material. The cage element is filled with a granular bone material. A drawback of this device is that the fusion between the granular bone material and the vertebral bodies must take place through the fibrous material of the cage element, and is therefore difficult to obtain. Moreover, in case of determined stress conditions, the cage element can explode. Furthermore, the device requires screws and rods, in order to fix the two adjacent vertebrae to each other, and to provide a primary stabilization; therefore it belongs to the instrument-assisted fusion devices, which are more difficult to be manufactured and implanted.

A cage-type device is also known as "Biocage", which is conceived for replacing a cervical vertebral disk and for providing a fusion of the vertebral bodies adjacent to the cervical vertebral disk. The device comprises a substantially tubular net cage element and a granular bone material arranged in the cage element. The cage element is open below and above so as to allow a contact of the granular material with the surface of the two vertebrae to be fused together. The cage element may be made of PET coated by a stiff reabsorbible polymer, e.g. PLLA.

Also this type of device very often fails to form a spinal fusion. As it is known, in fact, osteosynthesis requires that suitable forces are exerted on the bone material. Since the cage element is stiff, the loads of the vertebrae are to applied to the cage element instead of the granular bone material. Therefore, the bone material of the device is substantially free from mechanical stress and so it is not stimulated for fusing with the bone of the vertebrae.

Moreover, this device has the drawback of triggering foreign body reactions, because it comprises an excessive amount of polymer, although reabsorbible, in order to obtain a stiff structure.

The interspinous fusion devices limit the sole flexion-extension movement of the spine and only partially. On the contrary, the interspinous fusion devices do not substantially limit the relative lateral bending and torsion movements. Therefore, the interspinous fusion devices leave to the adjacent vertebrae a residual relative mobility, which disturbs or even hinders the fusion. In other words, the exclusive use of interspinous fusion devices cannot provide a primary stabilization that develops into a fusion.

Accordingly, the need is felt of a device for fusion of two adjacent vertebrae comprising a bone fusion material that, once implanted, enables the two vertebrae to mechanically stimulate the fusion of the bone material and that hinders the relative mobility of the two vertebrae immediately after implanting the device, providing a primary stabilization required for the fusion to develop, overcoming the drawbacks of the prior art.

US 2008/167686 A1 describes an intervertebral spacer device comprising a container consisting of two compression resilient elements, in particular leaf springs. In an exemplary embodiment, the container has two open end portions. A procedure is also described in which the spacer device is filled with a material adapted to promote bone growth, substantially for fixing it in its implant site.

WO2009/005819 describes an intervertebral device for providing a "mobile fusion" of two adjacent vertebrae, i.e. for forming a connection of the vertebrae in which an elastic relative mobility is enabled therebetween. In fact, exemplary embodiments are described that are expressly conceived to allow at least two vertebral movement modes selected among the flexion-extension movement, the lateral bending movement and the axial rotation movement.

Both devices include contact portions, designed to come into contact with the vertebral bodies, which resiliently react to the forces exerted by the vertebral bodies. The bone growth promoting material cannot do more than fixing the contact portions to the respective vertebral bodies, but it cannot stiffen the device and, therefore, it cannot immobilize the two vertebrae to each other. In fact, in the former case, the compression movement of the container does not enable a primary stabilization and, accordingly, the fusion of the two vertebral bodies. In the latter case, the relative mobility of the vertebral bodies is expressly wanted.

Therefore, both such devices embody substantially an intervertebral disc prosthesis and are not used to form a vertebral fusion in the true sense.

It is also observed that the container of US 2008/167686 A1 cannot be filled with an osteosynthesis material, in particular with bone material, in the granular form.

SUMMARY OF THE INVENTION

It is therefore an object of the present invention to provide a device for forming a fusion of two adjacent vertebrae comprising a bone fusion material, which is arranged to be subjected to forces exerted by the vertebrae in order to stimulate the fusion process.

It is also an object of the invention to provide a fusion system that hinders the relative movements of the two vertebrae thus providing a primary stabilization that promotes a prompt fusion of the two vertebrae, without using any primary stabilization means such as screws and plates.

It is also an object of the present invention to provide such a device and system that can be implanted by an easy and minimally invasive procedure.

It is also an object of the present invention to provide such a device and system that can be easily and quickly manufactured.

These and other objects are achieved by a vertebral fusion device comprising a support element configured for insertion between two corresponding vertebral portions of two adjacent vertebrae of a patient's spine portion, said corresponding vertebral portions comprising processes and/or joint surfaces of the adjacent vertebrae, such that a supporting reaction is provided to said corresponding vertebral portions, wherein the support element is axially compliant along the direction of the axis, the main feature of which is that the support element comprises:

a plastically deformable granular osteosynthesis material;

a hollow container body having a side wall and two open end portions, the hollow container body containing the granular osteosynthesis material, so as to allow a direct contact of the granular osteosynthesis material with said two corresponding vertebral portions through the open end portions and so that the container laterally contains the granular osteosynthesis material and makes it possible a plastic deformation thereof in an axial direction between the two open end portions until the granular osteosynthesis material forms a continuous pillar between said corresponding vertebral portions along the axial direction, and the side wall arranged to yield along the axial direction following the plastic deformation of the granular osteosynthesis material.

This way, the loads of said corresponding vertebral portions is applied only to the granular bone material that forms the pillar, and not to the container body, which is axially compliant. In these conditions, once the fusion device has been implanted, the granular bone material supports the loads exerted by said corresponding vertebral portions between which it is arranged, and at the same time receives a compression force that stimulates the bone fusion process, and so the formation of an arthrodesis is assured.

Moreover, due to the granular nature of the bone material, unlike an axially prior art stiff fusion device, this fusion is configured for somewhat dampening the impulsive loads and the vibrations that may occasionally or systematically be transmitted by said corresponding vertebral portions. This improves the stability of the vertebral bodies and the comfort to the patient.

Moreover, with such a device, the granular bone material and/or fragments in the hollow container body cannot be dispersed in the patient's body, in case of failed fusion.

Besides, as it will be shown hereinafter, the fusion device according to the invention can be implanted by a minimally invasive technique.

In a preferred exemplary embodiment, the side wall of the hollow container body is substantially inextensible in a transversal direction. This way, the granular material cannot expand radially, and remains in an overall compression condition.

In an exemplary embodiment, the hollow container body comprises a couple of substantially symmetrical longitudinal shells. In particular, the shells are connected along respective segments longitudinal. Such makes it easier to prepare the hollow container body starting from a plane article.

In an exemplary embodiment, the fusion device is configured for insertion into an interspinous space, i.e. into a space between a lower surface of the spinous process of the upper vertebra of the two adjacent vertebrae and the upper surface of the spinous process of the lower vertebra, wherein the fusion device has upper and lower end portions configured for abutting to these lower and upper surfaces, respectively, in order to obstruct the interspinous space. Such fusion device is indicated hereinafter as an interspinous fusion device or as a fusion interspinous device.

Preferably, the interspinous fusion device has a height set between 6 mm and 18 mm, in particular between 9 mm and 15 mm.

Advantageously, the interspinous fusion device comprises an interlaminar front part configured for positioning between respective laminae of the upper and lower adjacent vertebrae. This interlaminar front part makes it possible to more safely block the flexion-extension movement of the spine portion comprising the two adjacent vertebrae, and to prevent them from becoming kyphotic.

The interspinous fusion device, possibly provided with the interlaminar front part, advantageously consists of a couple of longitudinal shells as indicated above, wherein each longitudinal shell has a respective upper profile and a respective lower profile configured for complying with the lower surface of the spinous process of the upper vertebra and with the upper surface of the spinous process of the lower vertebra of the two adjacent vertebrae, respectively, and preferably an upper face of the spinous processes of the upper vertebra and of the lower vertebra, respectively, which may be configured for complying with the laminae of the upper vertebra and of the lower vertebra, respectively.

Advantageously, the fusion device comprises a bilateral constraint means configured for engaging with the spinous processes, in order to keep the granular osteosynthesis material in a compressed condition between the spinous processes.

In particular, the bilateral constraint means comprises a ligament configured for fastening the interspinous fusion device to the spinous processes.

The side wall of the fusion devices has a substantially cylindrical shape. In particular, this cylindrical shape has a substantially elliptical cross section, more in particular, the cylindrical shape has a substantially circular cross section. In particular, such fusion device is configured for insertion between two mutually facing joint surfaces of the vertebral bodies, or between two cooperating articular facets, or between two transverse processes of the adjacent vertebrae.

In an exemplary embodiment, the fusion device is configured for insertion into an intersomatic space between two mutually facing joint surfaces of said two vertebral bodies. This fusion device is indicated hereinafter as an intersomatic vertebral fusion device or as a fusion intersomatic device. Preferably, this vertebral fusion intersomatic device has a height set between 5 mm and 20 mm, in particular between 5 mm and 15 mm, and a transversal dimension, in particular a diameter, set between 5 mm and 15 mm.

In an exemplary embodiment, the fusion device is configured for insertion between two cooperating articular facets of the two adjacent vertebrae. Such fusion device is indicated hereinafter as an interarticular vertebral fusion device or as a fusion interarticular device. Preferably, this fusion interarticular device has a height set between 5 mm and 14 mm, in particular between 5 mm and 10 mm. With these sizes, the intersomatic device, more in particular, a plurality of intersomatic devices, as described hereinafter, can be inserted into the housing between the vertebral bodies of the two adjacent vertebrae.

In an exemplary embodiment, the fusion device is configured for insertion between two corresponding transverse processes of the two adjacent vertebrae. Such fusion device is indicated hereinafter as an intertrasverse vertebral fusion device or as a fusion intertrasverse device. Preferably, said intertrasverse device has a height set between 15 mm and 45 mm, in particular to between 25 mm and 40 mm, and a transversal dimension, in particular a diameter, set between 5 and 15 mm.

The side wall of the hollow container body can comprise a cage element, i.e. an element having a reticular structure. In particular, this cage element comprises a network that has interlaced meshes, wherein said meshes have size configured for containing the granular material. The interlaced meshes structure can be easily manufactured from a plane article, by longitudinally joining a strip of interlaced network to itself.

As an alternative, the cage wall of the hollow container body may comprise a spiral-shaped structure. As an alternative, or in addition, the hollow container body may comprise a fibrous structure. As an alternative, or in addition, the hollow container body may comprise a composite structure.

The hollow container body may be made of a biocompatible material such as polyethylene terephthalate, titanium, PEEK, carbon fibre or a combination thereof.

The fusion devices according to the invention have a lower height set between a minimum value and a maximum value, depending upon the implant site.

Advantageously, the fusion device is in an axially precompressed configuration from a rest position to a precompressed position, wherein a wrapper is provided to keep the fusion device at the precompressed position.

In another aspect of the invention, the above indicated objects are reached by a vertebral fusion system comprising a plurality of vertebral fusion devices that have the above indicated features, wherein the vertebral fusion devices are selected from the group consisting of:
   an intersomatic fusion device, i.e. a device configured for insertion between two mutually facing joint surfaces of the two vertebral bodies;
   an interspinous fusion device, i.e. a device configured for insertion between the two spinous processes of the adjacent vertebrae;
   an interarticular fusion device, i.e. a device configured for insertion between two cooperating articular facets of the adjacent vertebrae;
   an intertrasverse fusion device, i.e. a device configured for insertion between two corresponding transverse processes of the adjacent vertebrae, in particular the system comprises a couple of fusion devices for insertion between respective couples of corresponding right and left transverse processes.

In an exemplary embodiment, the system comprises an interspinous fusion device, at least one intersomatic fusion device and a couple of interarticular fusion devices for insertion between respective couples of cooperating articular facets.

The fusion system according to the invention makes it possible to make an implant that can provide a primary stabilization, so as to promote bone fusion, without using a means such as screws or fastening rods for mutually fastening the adjacent vertebrae.

More in detail, the interspinous fusion device alone can at least partially hinder the relative flexion-extension movement of the two adjacent vertebrae. The intersomatic fusion device makes it possible to completely block the relative flexion-extension movement. The interarticular fusion devices, to be preferably used as a couple, makes it possible to hinder also the relative lateral bending and torsion movements of the two adjacent vertebrae. Therefore, the system according to the invention can provide a high contact surface, and suppress all the components of the relative movement of the two adjacent vertebrae. Such an arthrodesis can be called a circumferential arthrodesis, i.e. an arthrodesis comprising a plurality of distinct elements, each of which cooperates to eliminate a specific degree of freedom of the relative movement of the adjacent vertebrae.

This way, the system provides a primary stabilization strong enough to ensure the completion of the fusion process. On the contrary, an excessive residual mobility, after the implant, would make the fusion difficult or even impossible. This happens in the fusion "cage" devices of the prior art, which can suppress one or at most two components of the flexion-extension, lateral bending, torsion movement.

In some instances, the complementary fusion devices, which are positioned between the right and/or left transverse processes, can be useful for hindering the relative movement of the adjacent vertebrae.

The system according to the invention, comprising the above described devices, allows combining a severe or total limitation of the relative movement after the implant and an availability of the granular bone material to be stimulated in a condition in which forces are exerted in a controlled way by the vertebral portions among which the devices are arranged. This condition promotes the fusion process and, therefore, the accomplishment of the arthrodesis.

In a preferred exemplary embodiment, the vertebral fusion system comprises at least one front intersomatic fusion device and at least one posterior intersomatic fusion device, which are configured for being placed at positions comprising front positions and rear positions within the intervertebral space, respectively, wherein the or each front device is preferably than the or to each rear device. This serves for forming an arthrodesis without causing the spine segment comprising the two adjacent vertebrae to become kyphotic. In particular, this fusion system comprises two rear intersomatic fusion devices and one front intersomatic fusion device.

The granular osteosynthesis material of the device according to the invention may be human or animal bone material, in particular bank bone.

Advantageously, this granular osteosynthesis material is in the form of tablets i.e. of chips that comprise cortical bone material and trabecular bone material in a prefixed proportion. The trabecular bone material is particularly prone to bone fusion, therefore it promotes the formation of the arthrodesis.

The fusion device may also comprise bone growth factors. Preferably, these growth factors are configured for causing the filling material comprising the granular osteosynthesis material and the growth factors to form a gel material. For example, growth factors are provided in an amount of medullar and/or peripheral blood added to the granular osteosynthesis material.

The growth factors may be added when using the device, i.e. in a step of preparation of the implant.

In an exemplary embodiment, the device may comprise a substance, such as a protein, adapted to promote the osteosynthesis. This makes it possible to form the fusion in time much shorter than what is allowed by the bone contact and by the primary stabilization provided by the device.

Moreover, the invention relates to a process for preparing a fusion device as described above. This process is described hereinafter, along with a procedure for implanting the above device and system for the fusion of two adjacent vertebrae.

BRIEF DESCRIPTION OF THE DRAWINGS

The invention will be now shown with the description of exemplary embodiments thereof, exemplifying but not limitative, with reference to the attached drawings, in which.

DESCRIPTION OF A PREFERRED EXEMPLARY EMBODIMENT

Exemplary embodiments of the vertebral fusion system are described hereinafter, along with vertebral fusion devices of the system according to the invention.

Figure 1:
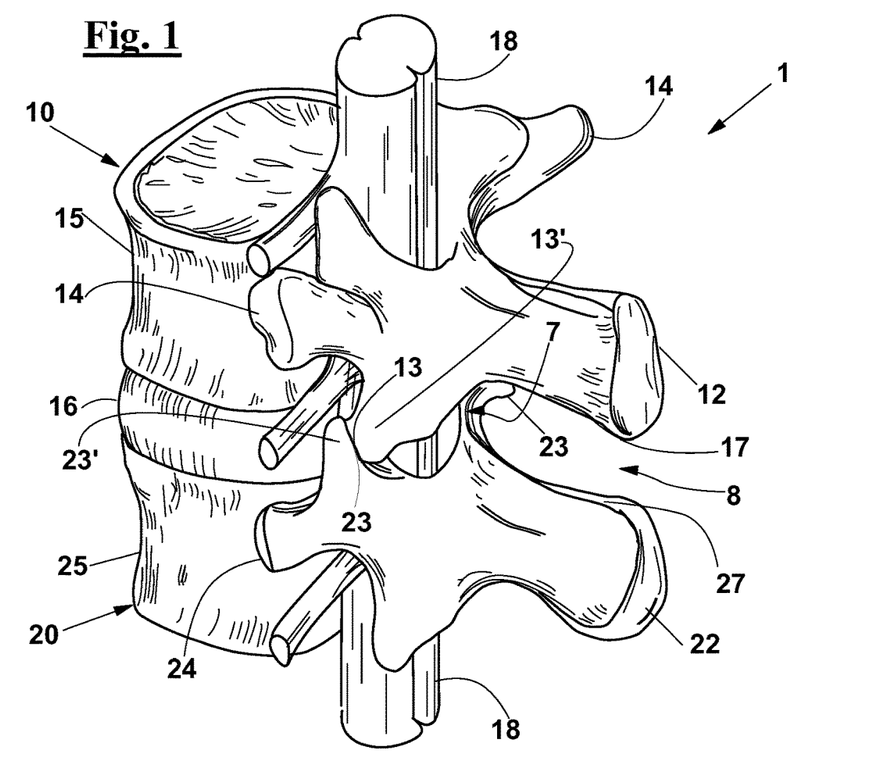
FIG. 1 is a perspective view of a lumbar segment of spine comprising two adjacent vertebrae.

The involved anatomical parts are indicated in FIG. 1, which shows a subject's spinal segment 1 comprising two adjacent lumbar vertebrae 10 and 20. However, the device according to the invention can be used to form a vertebral fusion at any spinal level, provided that modifications are made that are obvious for a skilled person.

Figure 2:
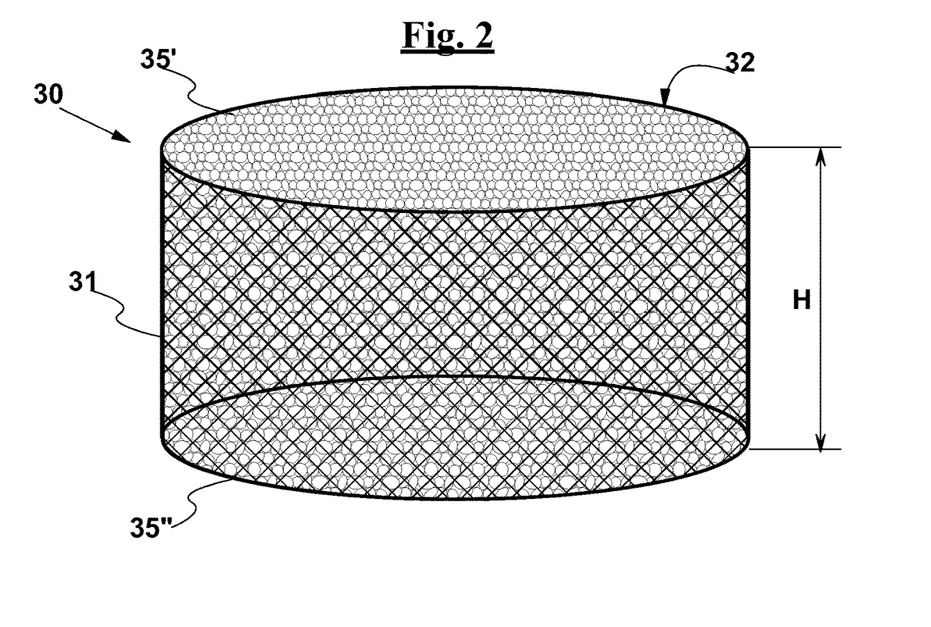
FIG. 2 is a perspective diagrammatical view of an intersomatic or interarticular fusion device, in a first exemplary embodiment.
Figure 3:
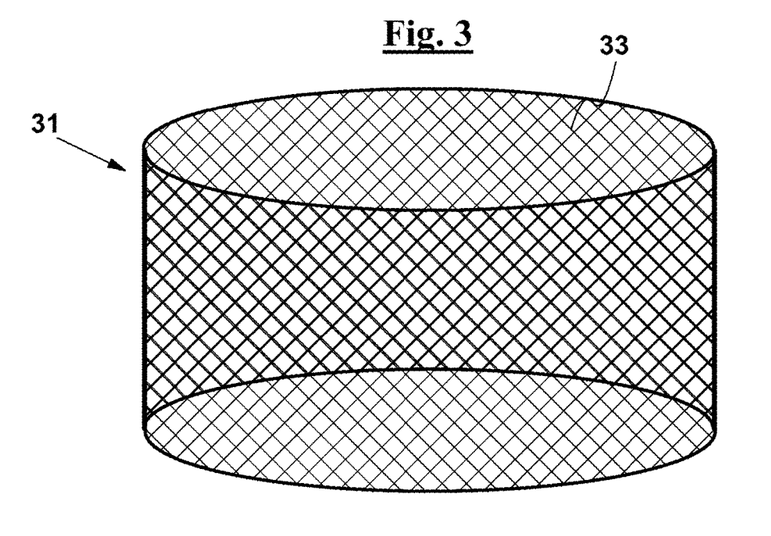
FIG. 3 is a perspective view of a hollow container body of the fusion device of FIG. 2.
Figures 4, 6:
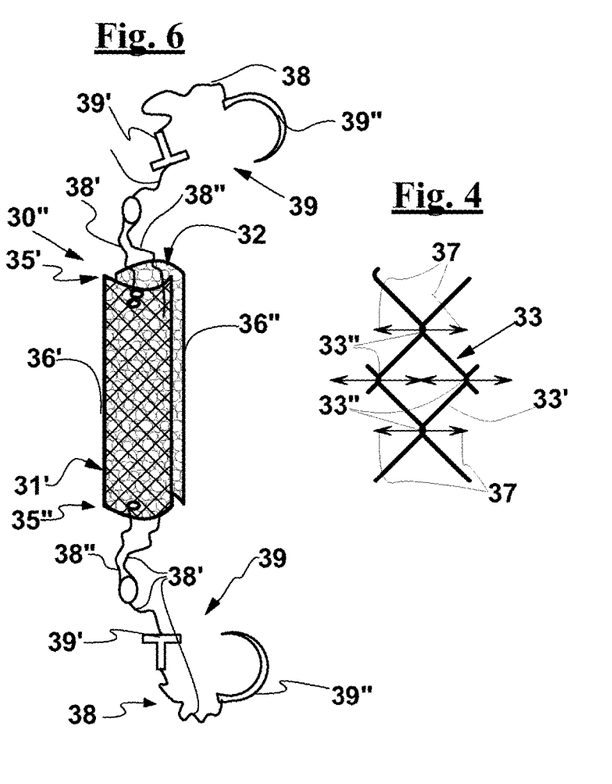
FIG. 4 shows a detail of the network of the hollow container body of FIG. 2.
FIG. 6 is a perspective diagrammatical view of a fusion interspinous device, according to a first exemplary embodiment of the invention.

With reference to FIGS. 2, 3 and 4, a vertebral fusion device 30 is described that comprises a support element including a hollow container body and a predetermined amount of a plastically deformable granular osteosynthesis material 32 arranged in hollow container body 31.

In the exemplary embodiment of FIG. 1, device 30 has a substantially cylindrical shape, in particular a cylindrical shape with a circular cross section.

Device 30 may have a height H so as to be configured for insertion between corresponding portions of adjacent vertebrae 10,20 (FIG. 1), in particular between two mutually facing joint surfaces 11,21 (FIG. 11) of vertebral bodies 15,25, in which height H is preferably set between 5 and 20 mm, in particular between 5 and 15 mm and, in a circular cross-section cylindrical device, the diameter is set between 5 and 15 mm. In other words, device 30 of FIG. 2 is configured for use as an intersomatic fusion device.

Device 30 may have a height H so as to be configured for insertion between two cooperating articular facets 13,23 of respective articular processes 13',23' (FIG. 14) of vertebrae 10,20, in which height H is preferably set between 5 and 14 mm, in particular between 5 and 10 mm. In other words, device 30 of FIG. 2 is configured for use as an interarticular fusion device.

FIG. 3 is a perspective view of hollow container body 31 of fusion device 30 of FIG. 2, without osteosynthesis material 32, according to an exemplary embodiment of the invention. Hollow container body 31 is manufactured starting from a reticular structure article such as a network 33 forming interlaced meshes, and comprises therefore a reticular structure cage element. A detail of network 33, is shown in FIG. 4, where net 33' is also depicted.

Figure 5:
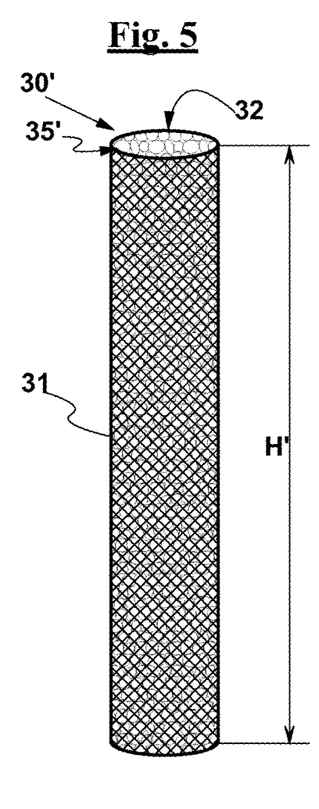
FIG. 5 is a perspective diagrammatical view of a fusion intertransverse device, according to a first exemplary embodiment of the invention.
Figure 13:
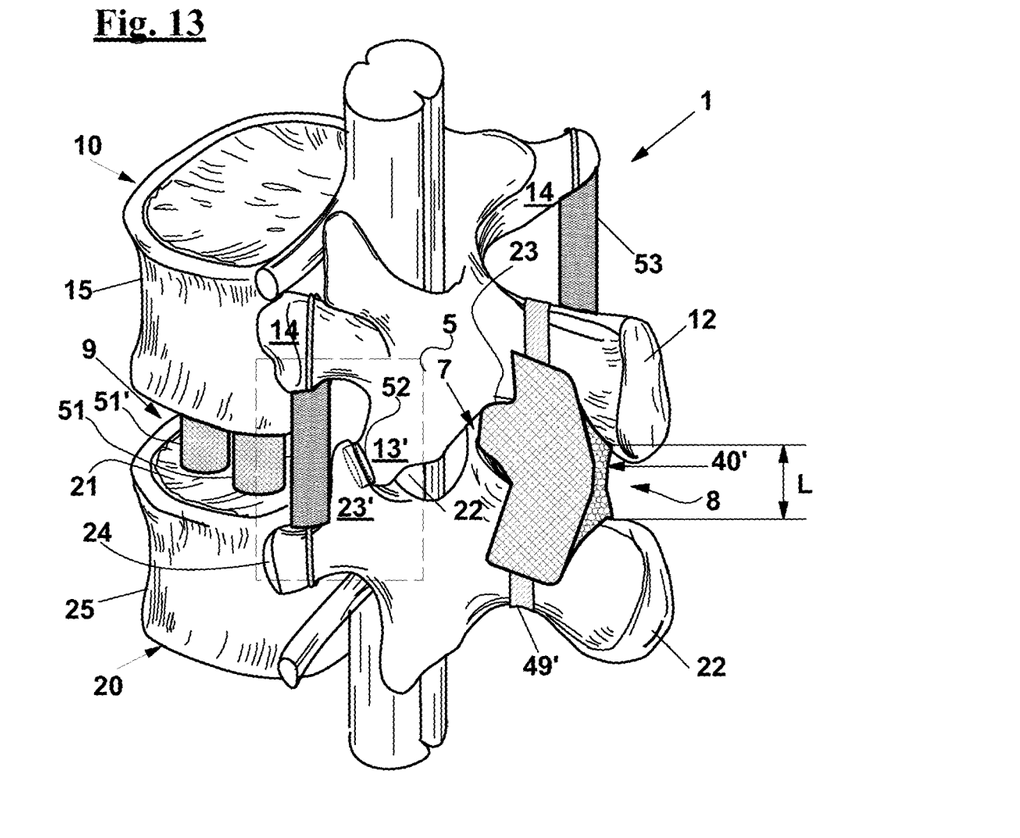
FIG. 13 is a postero-lateral perspective view of the segment of spine of FIG. 5 provided with the fusion devices shown in FIG. 12, and with intersomatic fusion devices.

FIG. 5 shows a fusion device 30' that has a height or length H' so as to be configured for insertion between two transverse processes 14,24 of adjacent vertebrae 10,20 (FIGS. 1 and 13). Preferably, height H' is set between 15 and 45 mm, in particular between 5 and 10 mm and, in a cylindrical device, the diameter is preferably set between 5 and 15 mm. Also fusion device 30' may include a hollow container body 31 comprising a network of interlaced meshes, which contains granular osteosynthesis material 32. In other words, device 30' of FIG. 5 is configured for use as an intertrasverse fusion device.

FIG. 6 shows another intertrasverse fusion device 30" configured for insertion between two transverse processes 14,24 of adjacent vertebrae 10,20 (FIGS. 1 and 13). Hollow container body 31', i.e. the side wall of hollow container body 31, comprises two shells 36' and 36" that are substantially symmetrical to each other and that, in the present exemplary embodiments, comprises two distinct shells. The two shells includes osteosynthesis material 32.

As still shown in FIG. 6, intertrasverse fusion device 30" may also be equipped with a constraint means 39 for engagement with transverse processes 14,24. The constraint means may also be provided for intertrasverse fusion device 30'. Constraint means 39 comprise, for each end 35,35" of device 30',30", a wire 38 including branches 38',38" that are connected at different points, in particular at diametrically opposite points, of end portions 35,35" (FIG. 5) of device 30',30". In the case of the two-shells hollow container body, branches 38',38" are connected to respective shells 36',36" of hollow container body 31. Constraint means 39 further comprises a wire-winding body 39' for wire 38, in order to adjust the length of wire 38, and also comprises a couple of anchor elements 39" that can be engaged with each other so as to tighten the wire. Constraint means 39 are configured for maintaining granular osteosynthesis material 32 in a compressed condition between transverse processes 14,24 (FIGS. 1 and 13).

Figures 7, 8:
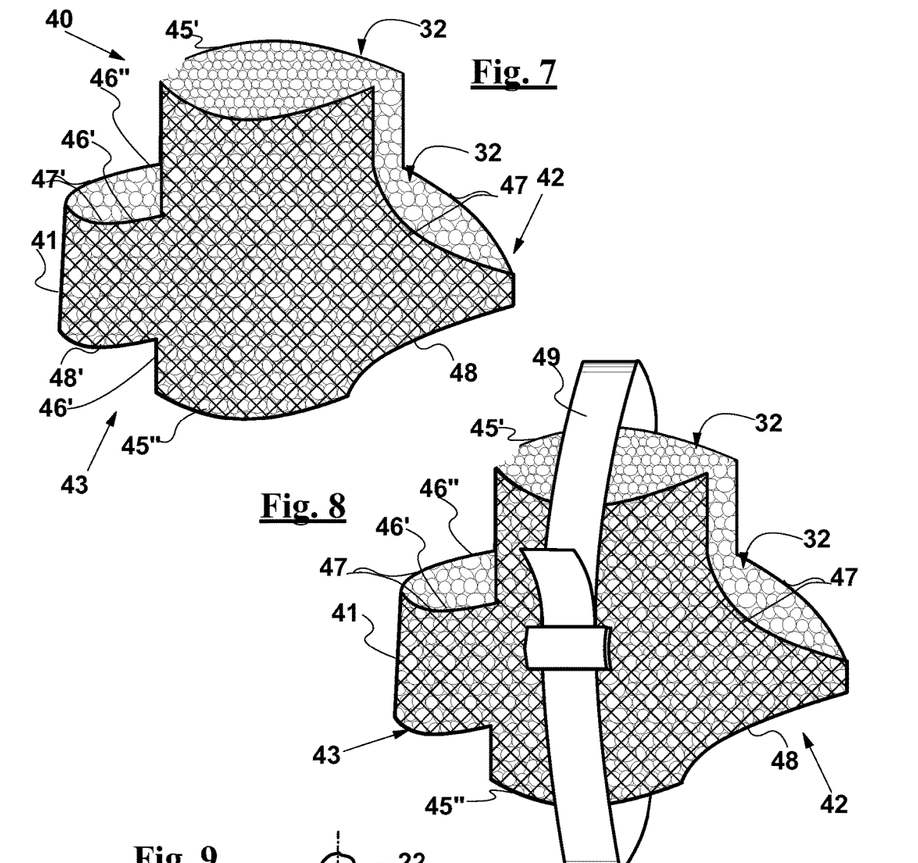
FIG. 7 is a perspective diagrammatical view of a fusion interspinous device, according to a second exemplary embodiment of the invention.
FIG. 8 is a perspective diagrammatical view of the interspinous fusion device of FIG. 7 that has a ligament arranged to lace with two adjacent vertebrae.

FIG. 7 shows a fusion device 40 configured for insertion through two spinous processes 12,22 of adjacent vertebrae 10,20 (FIGS. 1 and 13).

The interspinous device 40 comprises a rear part 42 configured for being positioned between two spinous processes 12,22. More in detail, interspinous device 40 comprises an upper portion 47 and a lower portion 48 that can be conformable to a lower surface 17 and to an upper surface 27 (FIG. 1) of two spinous processes 12,22, respectively, in order to obstruct an interspinous space 8 between two spinous processes 12,22, in order to form an interspinous arthrodesis.

In the exemplary embodiment as depicted, interspinous device 40 comprises a hollow container body 41 consisting of a left shell 46' and of a right shell 46" that are substantially symmetrical to each other, and that are joined longitudinally. Hollow container body 41 may be manufactured starting from a reticular structure article such as a network 33 of interlaced meshes. In this two-shells exemplary embodiment, each shell 46',46" has a respective upper profile 47 and a respective lower profile 48 that can be conformable to a lower surface 17 and to an upper surface 27 (FIG. 1) of two spinous processes 12,22, respectively.

Figures 10, 11:
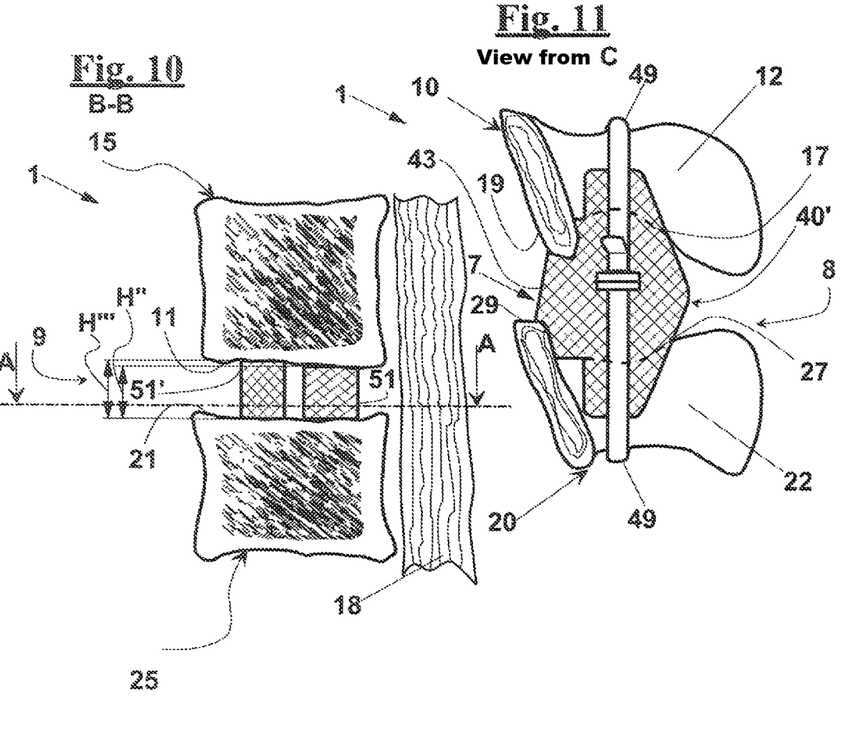
FIG. 10 is a partial longitudinal sectional view of the segment of spine of FIG. 1, taken at the vertebral bodies, in which the segment of spine is provided with intersomatic fusion devices according to the invention.
FIG. 11 is a partial elevational side view of the spinous processes of the segment of spine of FIG. 1 that is provided with an interspinous fusion device according to the invention, in particular with the fusion device of FIG. 7.

In the exemplary embodiment of FIG. 7, fusion device 40 may comprise a front part, i.e. an interlaminar part 43 that is configured for insertion between laminae 19,29 of adjacent vertebrae 10,20. This insertion is shown in FIG. 11, which relates to a device 40' (FIG. 8), described below, which comprises a hollow container body 41 similar to the body of device 40.

Interspinous fusion device 40' of FIG. 8 has the same structure as device 40 of FIG. 7, and also comprises a constraint means 49 for engagement with spinous processes 12,22. In this case, the constraint means includes a ligament 49 that is arranged to lace with two adjacent vertebrae 10,20, and serves therefore as bilateral constraint means with spinous processes 12,22, in order to maintain granular osteosynthesis material 32 in a compressed condition. More in detail, interlaminar part 40 comprises a higher profile 47' and a lower profile 48' that can be conformed to a lower surface and to an upper surface of laminae 19,29 (FIG. 11), respectively, so as to obstruct an interlaminar space 7 between two laminae 19,29, in order to form an interlaminar arthrodesis. In the two-shells exemplary embodiment of FIG. 7, each shell 46',46" has a respective upper profile 47' and a respective lower profile 48'. Constraint means 49 also contribute to contain the lateral extension of device 40', which has the above-mentioned advantages.

Advantageously, interspinous fusion device 40,40' has preferably a size, in particular a height L (FIG. 13), set between 6 mm and 18 mm, in particular between 9 mm and 15 mm.

In devices 30,30',30",40,40' shown in the figures described above, height H, H'.H", H''', L are selected to take into account the vertebral dimensions, which depend upon the build of the patient and upon the spinal level of adjacent vertebrae 10,20.

As shown in FIGS. 2-8, hollow container body 31,31',41 of the fusion devices has open upper end portions upper 35',45' and open lower end portions 35",45". In the exemplary embodiments as depicted, the openings extend over the whole end sections of container body 31,31',41. This way, as shown in FIGS. 10-13, granular osteosynthesis material 32 contained in hollow container body 31,31',41, after the implant, is arranged in contact with the surfaces of corresponding vertebral portions 11,21; 12,22; 13,23; 14,24 through open end portions 35,45',45".

Hollow container body 31,31',41 of devices 30,30',30", 40,40' has a side wall (FIGS. 3,5) that laterally contains the granular osteosynthesis material (32). The side wall of hollow container body 31,31',41 is axially compliant, under the action of an axial load that acts on vertebral fusion device 30,30',30",40,40'. In an exemplary embodiment, the side wall is also substantially inextensible in the radial direction, therefore in the circumferential direction. This feature can be obtained, for example, by making hollow container body 31,31',41 starting from a reticular structure article such as a network 33 of interlaced meshes 33', as shown in FIG. 3,4. Network 33 of interlaced meshes comprises meshes 33' defined by interlacement contact points 33", whose size is selected in such a way that the network is substantially inextensible under the action of radial forces 37 that arise due to the compression exerted by the vertebral surfaces on osteosynthesis material 32, and that tend to radially enlarge hollow container body 31,31',41. In alternative to the reticular structure, different structures are possible, for instance a spiral-shaped structure, as well as fibrous and composite structures, that aren't shown in the figures but can be easily used by a skilled person. Regardless of the selected structure, hollow container body 31,31',41 is made of a biocompatible material, in particular of a non-bioabsorbable material such as polyethylene terephthalate, Titanium, PEEK, carbon fibre.

Granular osteosynthesis material 32 of fusion device 30,30',30",40,40' according to the invention may be human bone or animal bone. In particular, the granular osteosynthesis material may comprise tablets, i.e. cortico-spongeous chips, which comprise both cortical bone material and trabecular bone material, in a prefixed proportion. In particular, the granular osteosynthesis material may derive from femur heads explanted from patients to whom a prosthesis has been implanted. In particular, donated human bone material may be used, or bone material coming from a bone bank can be used.

The filling material of fusion device 30,30',30",40,40', according to the invention, may also comprise growth factors, not shown, which are contained, for example, in medullar and/or peripheral blood added to granular osteosynthesis material 32. Besides assisting osteosynthesis, these growth factors can forming a jellified filling with granular osteosynthesis material 32. The addition of the growth factors can be carried out also when using the device, i.e. in a step of preparation of the implant.

With reference to FIGS. 9-14, a vertebral fusion system is described, according to the invention. The vertebral fusion system comprises an interspinous fusion device 40', a couple of interarticular devices 52 and one or preferably more intersomatic devices 51,51'. Interarticular devices 52 and intersomatic devices 51,51' may have the shape of device 30, and of devices 30' or 30", respectively, as described above.

Figure 9:
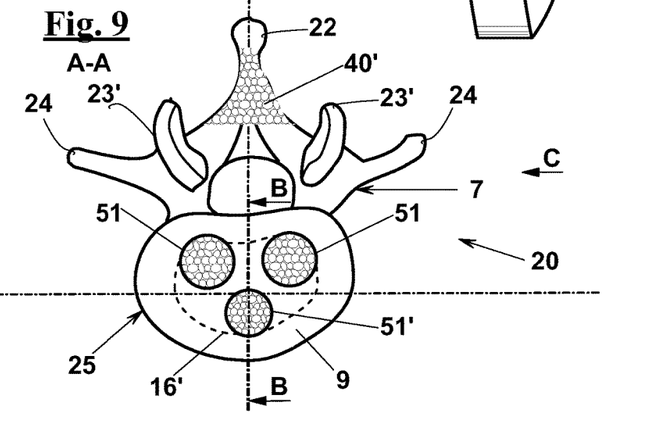
FIG. 9 is a cross sectional view of the segment of spine of FIG. 1 provided with a fusion device according to the invention.

FIGS. 9,10 and 13 show intersomatic devices 51,51' in use, arranged in an intervertebral space 9, typically in a zone 16' of the nucleus polposus of a vertebral disc 16 (FIG. 1), between mutually facing joint surfaces 11,21 of vertebral bodies 15,25 of adjacent vertebrae 10,20 (FIGS. 1 and 13). Intersomatic devices 51,51' are arranged to receive a compression load from joint surfaces 11,21, due to a distraction of two adjacent vertebrae 10,20 carried out before the implant. This way, granular bone material 32 (FIG. 2) receives compression loads from joint surfaces 11,21 which may change responsive to the patient's position and movements. These compression loads stimulate the fusion of granular osteosynthesis material 32 with intervertebral faces 11,21, until a continuous pillar is formed between them. In the exemplary embodiment of FIG. 9, two rear intersomatic devices 51 and a front intersomatic device 51' are provided. Rear devices 51 are located closer to vertebral arch 7, while front device 51 is arranged farther from it. Height H''' of front device 51' may be higher than height H'' of rear devices 51, as shown in FIG. 10, in order to more effectively contrast the reaction of interspinous device 40' to compression, and to more effectively prevent the segment of spine comprising vertebrae 10,20 from becoming kyphotic.

FIGS. 9 and 11-13 show interspinous fusion device 40' arranged within interspinous space 8 between spinous processes 12,22 of adjacent vertebrae 10,20. Interspinous fusion device 40' is arranged so that its own rear part 42 receives a compression load from upper surface 27 of lower spinous process 22, and from lower surface 17 of upper spinous process 12, in response to a distraction of two adjacent vertebrae 10,20 carried out before the implant.

In the exemplary embodiment of FIG. 11, interspinous fusion device 40' is also arranged in such a way that its own front part 43 receives a compression load from the upper surface of lamina 29 of lower vertebra 20, and from the lower surface of lamina 19 of upper vertebra 10. Artificial ligament 49, by which interspinous fusion device 40' can be fastened to spinous processes 12,22, may be configured for increasing the compression load. This way, granular bone material 32 (FIG. 8) receives substantially compressive loads, which changes responsive to the patient's position and movements. The compression loads stimulate the fusion of granular osteosynthesis material 32 with surfaces 17,27 of spinous processes 12,22 and, in this exemplary embodiment, of laminae 19,29, until a continuous pillar is formed between said corresponding vertebral portions. Preferably, surfaces 17,27 of spinous processes 12,22 expose trabecular bone material 32. This is possible by preliminarily removing the cortical bone material of surfaces 17,27 of the spinous processes and, in the embodiment of device 40', of laminae 19,29, for instance, by a common bone milling cutter.

FIGS. 9-13 also show implants comprising single fusion devices according to the invention, in particular comprising intersomatic devices 51,51', interarticular devices 52, an interspinous device 40' and intertrasverse devices 53. The devices of a given type can be implanted independently, and/or they may have a different structure with respect to the other devices. In other words, for instance, intersomatic devices 51,51' according to the invention may be advantageously implanted together with an interspinous device, according to the invention or not, which is different from interspinous device 40'. Similarly, interspinous device 40' according to the invention may be advantageously implanted with at least one intersomatic devices, according to the invention or not, which is different from fusion intersomatic devices 51,51' of FIG. 13.

Figure 12:
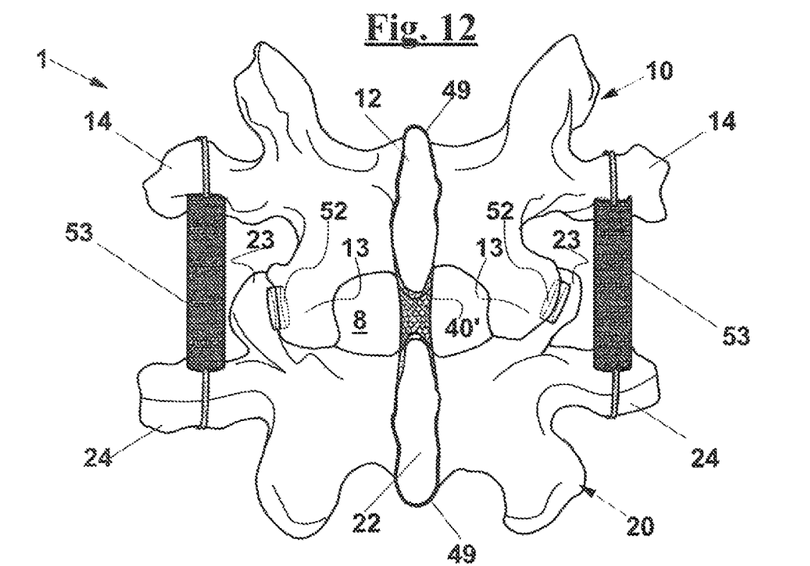
FIG. 12 is a rear view of the segment of spine of FIG. 10 provided with a couple of intertrasverse fusion devices, with a couple of interarticular devices and with an interspinous device.
Figure 14:
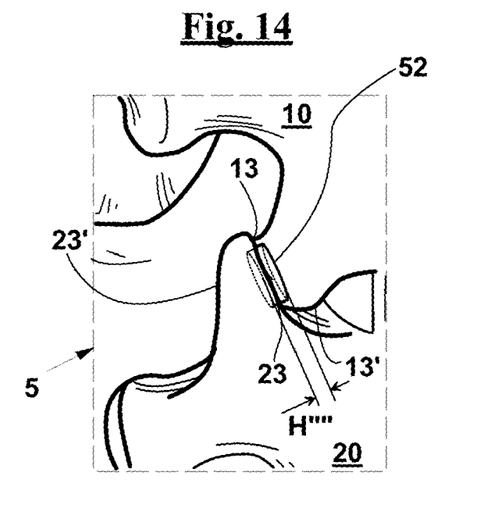
FIG. 14 is an enlarged portion of the view of FIG. 13, which shows more in detail, a couple of articular facets with an interarticular fusion device therebetween.

As shown in FIGS. 12-14, each interarticular fusion device 52 is located between facets 13,23 of a respective couple of cooperating articular facets, i.e. of a respective couple of mutually engaging articular facets of adjacent vertebrae 10,20. Even in this case, interarticular devices 52 are arranged to receive a compression load from articular facets 13,23. This way, granular bone material 32 (FIG. 2) receives substantially compressive loads which change responsive to the patient's position and movements. These compression loads stimulate the fusion of granular osteosynthesis material 32 with articular facets 13,23, until a continuous pillar is formed between them, which hinders their mutual slide movement and therefore prevents the lateral bending and torsion movements of two adjacent vertebrae 10,20.

FIG. 14 shows a detail of the region 5 of articular processes 13',23', provided with fusion devices 52. For the sake of clearness, fusion devices 51,52, which are shown in FIG. 13, are omitted in FIG. 14. The positioning of device 52 between cooperating articular facets 13,23 requires a housing to be preliminarily created between facets 13,23, which is obtained by removing the connective tissue and a portion of bone material at the end of articular processes 13',23' of adjacent vertebrae 10,20, at facets 13,23.

With reference to FIGS. 12,13, a fusion device according to the invention may comprise a couple of intertrasverse devices 53 in addition to the intersomatic, interarticular and interspinous devices. Each intertrasverse device 53 is located between two transverse processes 14,24 of a couple of right or left transverse processes of adjacent vertebrae 10,20. Intertransverse device 53, which is typically a complementary device, may be made as shown in FIG. 5 or in FIG. 6. In FIG. 5, hollow container body 31 is a continuous tubular body, while in FIG. 6, hollow container body 31 is a continuous tubular body consisting of two halves that can be joined together at a joining line. Even in this case, intertrasverse devices 53 are arranged to receive a substantially compressive load from transverse processes 14,24. This way, granular bone material 32 (FIGS. 5,6) receives substantially compressive loads which change responsive to the patient's position and movements. The compression loads stimulate the fusion of granular osteosynthesis material 32 with transverse processes 14,24, until a continuous pillar is formed between them, which makes it possible to hinder the relative movement of two adjacent vertebrae 10,20 and assists the primary stabilization.

FIGS. 15 to 18 show a toolkit for implanting the fusion device.

Figures 15, 16, 17, 18:
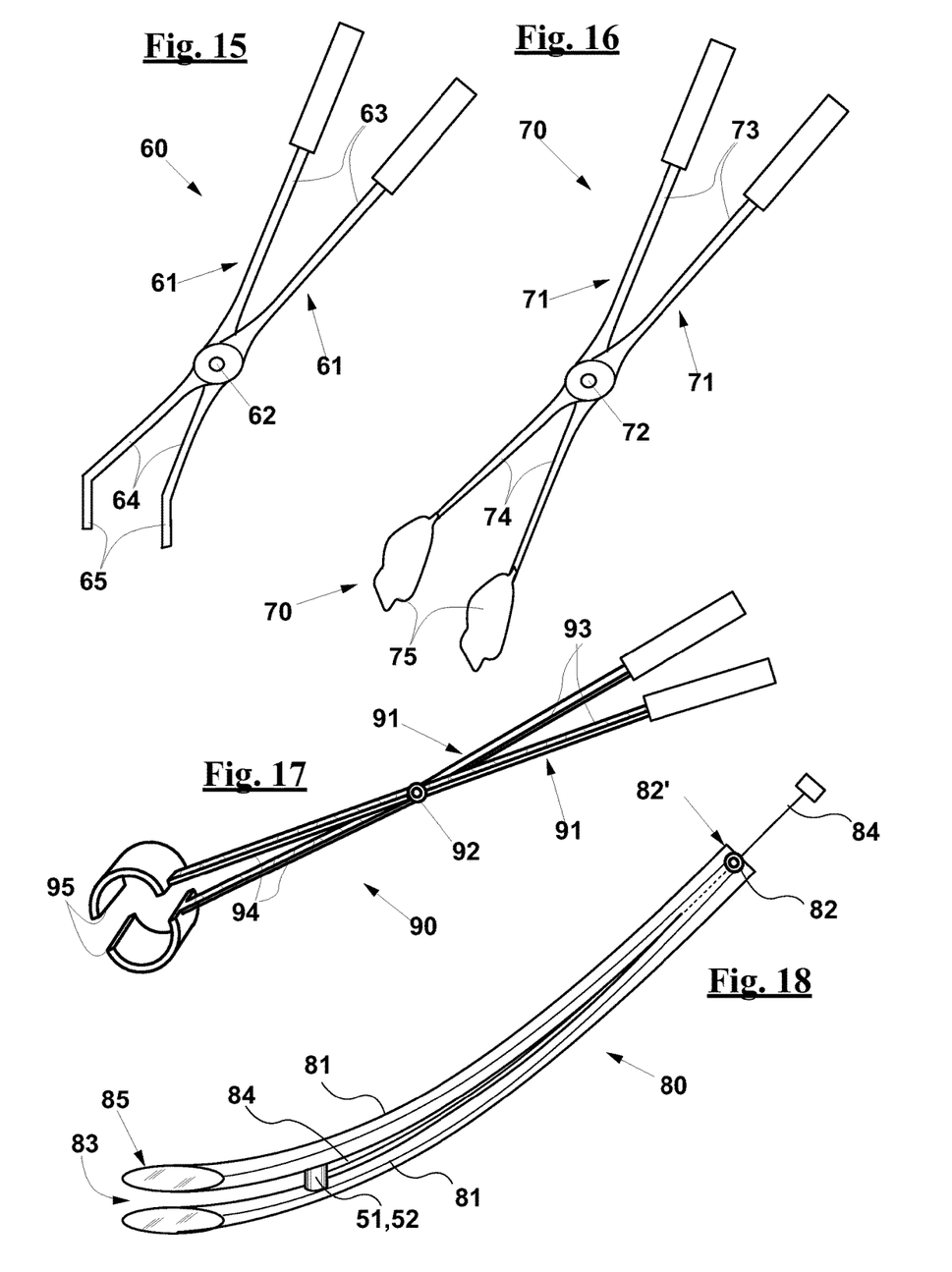
FIG. 15 is a perspective view of a distraction device for preparing a couple of adjacent vertebrae to receive a device according to the invention.
FIG. 16 is a perspective view of a forceps for implanting the interspinous fusion device according to the invention.
FIG. 17 is a perspective view of a forceps for implanting the fusion intertrasverse device according to the invention, and of a fusion intertrasverse device according to the invention.
FIG. 18 is a perspective view of an injection device for implanting the intersomatic fusion device and the interarticular fusion device according to the invention.

FIG. 15 shows a distraction device 60 for causing a distraction of adjacent vertebrae 10,20 before introducing and positioning at least one intersomatic device 51,51' into intervertebral space 8 (FIG. 13), to replace the nucleus polposus of intervertebral disc 16. Distraction device 60 has the structure of a reverse action forceps, and comprises two substantially linear halves 61 connected to each other at a pivot point 62, so as to define a working plane of the two halves 61. Each half 61 of distraction device 60 comprises a handle portion 63 and a working portion 64. Working portion 64 globally comprises two insertion portions 65 that are substantially orthogonal to the working plane. In order to cause the preliminary distraction of adjacent vertebrae 10,20, the distraction device is positioned between spinous processes 12,22 (FIG. 1), which are spaced apart by applying an opening force to the handle portions 63 of distraction device 60.

FIG. 16 shows a forceps 70 for positioning interspinous fusion device 40 or 40' into interspinous space 8 (FIG. 1). Forceps 70 has the structure of a direct action forceps, and comprises two substantially linear halves 71 connected to each other at a pivot point 72, in order to define a working plane of the two halves 71. Each half 71 of forceps 70 comprises a handle portion 73 and a working portion 74. Working portion 74 globally comprises two flat grip devices 75 that are configured to contain interspinous fusion device 40 or 40', in order to apply and to maintain an axial compression on granular osteosynthesis material 32. The flat grip devices are configured for insertion into interspinous space 8 and for releasing fusion device 40 or 40' in this space.

FIG. 17 shows a forceps 90 for positioning an intertrasverse fusion device 30 or 30' (FIGS. 2,5) into the space between two transverse processes 14,24 (FIG. 1) of respective adjacent vertebrae 10,20. Forceps 90 has the structure of a direct action forceps, and comprises two substantially linear halves 91 connected to each other at a pivot point 92, in order to define a working plane of the two halves 91. Each half 91 of forceps 90 comprises a handle portion 93 and a working portion 94. Working portion 94 globally comprises two curved grip devices 95, in particular cylindrical devices, that are configured to contain an interspinous fusion device 30 or 30'.

FIG. 18 shows an injection device 80 for positioning fusion intersomatic devices 51,51' (FIGS. 2,5) in intervertebral or intersomatic space 9 between vertebral bodies 15,25 of adjacent vertebrae 10,20, and for positioning fusion interarticular devices 52 between articular facets 13,23 of vertebral bodies 15,25 of adjacent vertebrae 10,20 (FIGS. 13 and 14). Injection device 80 consists of two halves 81 connected to each other at a pivot point 82 at one manoeuvre end portion 82'. Two halves 81 define a housing 83 that is configured for slidingly receiving and for retaining an intersomatic or an interarticular fusion device 51,51',52. A hole, not shown, is provided at manoeuvre end portion 82' for moving a linear guide device 84, in particular a Kirschner wire 84, in order to cause intersomatic or interarticular fusion device 51,51',52 slide along injection device 80, up to one release end 85 opposite to manoeuvre end portion 82', which is configured to be positioned in intersomatic space 9 and in the housing between articular facets 13,23.

A procedure for preparing a fusion device 30,30',40,40', 51,51',52,53, according to the invention, may comprise the steps of:

prearranging hollow container body 31,31',41 (FIGS. 3-6) that has prefixed shape and size;

prearranging an amount of granular osteosynthesis material 32, in particular an amount of a granular bone material;

filling hollow container body 31,31',41 with granular osteosynthesis material 32, possibly by applying a compression force on granular osteosynthesis material 32. The amount of granular osteosynthesis material 32, and the way to fill hollow container body 31,31',41 with, is selected by taking into account that the bone undergoes a step of reabsorption in an initial step the implant, which causes a certain shrinkage;

advantageously, adding additives to granular osteosynthesis material 32, in particular adding active principles and/or of bone growth factors, not shown, to promote osteosynthesis;

under vacuum arranging fusion device 30,30',40,40',51, 51',52,53 in a sterile bag, not shown.

As already described, fusion device 30,30',40,40',51,51', 52,53 according to the invention may be produced in a precompressed state. In other words, in the preparation procedure, a step may be provided in which the fusion device, comprising hollow container body 31,31',41 and osteosynthesis material 32, is brought from a rest position or configuration to a precompressed position or configuration. A step may also be provided in which fusion device 30,30', 40,40',51,51',52,53 is contained within a wrapper, not shown, for example the above mentioned an under-vacuum sterile bag, configured for maintaining the side wall axially precompressed in the precompressed state.

Hereinafter, procedures are described for implanting devices 30,30',40,40',51,51',52,53 of a vertebral fusion system according to the invention.

These vertebral fusion devices may be implanted through a medial or side approach. More in detail, a procedure for implanting a system comprising at least one intersomatic devices 51,51', a couple of interarticular devices 52 and an interspinous device 40 or 40', comprises the steps of:

forming a first cutaneous access at a spine segment comprising two adjacent vertebrae 10,20 (FIG. 1);

cutting and locally removing the yellow ligament, not shown, over an interspinous space 8 between two vertebrae 10,20, through the first cutaneous access;

moving a portion of the spinal cord 18 between two vertebrae 10,20, in order to display disc 16 between two vertebrae 10,20;

removing the nucleus of intervertebral disc 16;

introducing and positioning intersomatic device 51,51' or intersomatic devices 51,51' at the same place of the nucleus of intervertebral disc 16 through the first cutaneous access;

introducing and positioning a first interarticular device 52 between two cooperating articular facets 13,23 of respective articular processes 13',23';

introducing and positioning an interspinous device 40,40';

forming a second cutaneous access;

introducing and positioning a second Interarticular device 52 through the second cutaneous access.

As an alternative, in another procedure for implanting such a system for arthrodesis an access side is not used for introducing and positioning interspinous device 40,40', and comprises the steps of:

forming a medial rear access of about 4-5 cm;

cutting and locally removing the yellow ligament, not shown, over an interspinous space 8 between vertebrae 10,20, through the medial rear access;

moving the dural sac, not shown, in order to display intervertebral disc 16 between vertebrae 10,20;

piercing intervertebral disc 16;

emptying the nucleus of intervertebral disc 16;

introducing and arranging at least one intersomatic device, which can comprise for example three intersomatic devices 51,51', of which two devices 51 to be arranged posteriorly and a device 51' to be arranged frontally within intersomatic space 9 between joint surfaces 11,21 of bodies 15,25 of two adjacent vertebrae 10,20;

preparing the surfaces of two cooperating articular facets 13,23. Such preparation step may comprise removing surface tissues, in particular the cartilage. This may be easily carried out by a conventional tool;

positioning interarticular device 52 between cooperating articular facets 13,23;

restoring the position of the dural sac;

preparing the surface of the spinous process 12,22, in order to expose the trabecular bone material of the spinous process;

introducing and positioning interspinous device 40,40';

possibly blocking interspinous device 40,40' by artificial ligament 49.

This way, a circumferential arthrodesis of two adjacent vertebrae 10,20 is obtained through an opening that may advantageously have a length of about 4-5 cm, and that allows a minimally invasive operation.

The step of preparing joint surfaces 13,23 may comprise removing the surface tissues, in particular the cartilage. This can be easily carried out by a conventional tool.

A procedure for implanting the fusion system according to the invention may comprise a step of compressing each device from a rest position to a precompressed position and, in order to enhance the compression forces that, once the device has been positioned, are applied on the granular osteosynthesis material.

The foregoing description of specific exemplary embodiments of the fusion device according to the invention, of a procedure for its preparation and for its implant, will so fully reveal the invention according to the conceptual point of view, so that others, by applying current knowledge, will be able to modify and/or to adapt in various applications the specific exemplary embodiments without further research and without parting from the invention, and, accordingly, it is meant that such adaptations and modifications will have to be considered as equivalent to the specific embodiments. The means and the materials to realise the different functions described herein could have a different nature without, for this reason, departing from the field of the invention. It is to be understood that the phraseology or terminology that is employed herein is for the purpose of description and not of limitation.

The invention claimed is:

1. A vertebral fusion device comprising:
a support element configured for insertion between two corresponding vertebral portions of two adjacent vertebrae of a patient's spine portion, wherein said corresponding vertebral portions comprise processes and/or joint surfaces of said adjacent vertebrae, such that a supporting reaction is provided to said corresponding vertebral portions,
wherein said support element comprises:
a plastically deformable granular osteosynthesis material;
a hollow container body having a side wall and two open end portions, said hollow container body arranged to contain said granular osteosynthesis material, and to allow a direct contact of said granular osteosynthesis material with both said corresponding vertebral portions through said open end portions, said hollow container body arranged to laterally contain said granular osteosynthesis material, and to allow a plastic deformation thereof in an axial direction between said two open end portions until said granular osteosynthesis material forms a continuous pillar between said corresponding vertebral portions along said axial direction, said side wall arranged to yield along said axial direction following the plastic deformation of said granular osteosynthesis material;
wherein said side wall comprises a cage element having a reticular structure.

2. The fusion device according to claim 1, wherein said side wall of said hollow container body is substantially inextensible in a transversal direction.

3. The fusion device according to claim 1, wherein said hollow container body comprises a couple of substantially symmetrical longitudinal shells.

4. The fusion device according to claim 1, configured for insertion into an interspinous space, defined as a space between a lower surface of a spinous process of an upper vertebra of said adjacent vertebrae and an upper surface of a spinous process of a lower vertebra of said adjacent vertebrae, wherein said fusion device has upper and lower end portions configured for conforming to said lower surface and to said upper surface, respectively, in order to obstruct said interspinous space.

5. The fusion device according to claim 4, comprising an interlaminar part configured for being positioned between a couple of laminae of said adjacent vertebrae, in order to obstruct an interlaminar space between said couple of laminae.

6. The fusion device according to claim 4, comprising bilateral constraint means configured for engaging said spinous processes, in order to keep said granular osteosynthesis material in a compressed condition between said spinous processes.

7. The fusion device according to claim 1, wherein said side wall has a substantially cylindrical shape.

8. The fusion device according to claim 1, configured for insertion into an intersomatic space set between two joint surfaces mutually facing two vertebral bodies respectively of said two adjacent vertebrae, wherein said vertebral fusion device has:
a height H", H''' set between 5 mm and 20 mm;
a transversal dimension set between 5 mm and 15 mm.

9. The fusion device according to claim 1, configured for insertion between two cooperating articular facets, wherein said fusion device has a height H'''' set between 5 mm and 14 mm.

10. The fusion device according to claim 1, configured for insertion between two corresponding transverse processes, wherein said fusion device has:
a height H' set between 15 mm and 45 mm;
a transversal dimension set between 5 mm and 15 mm.

11. The fusion device according to claim 1, wherein the reticular structure is a network comprising interlaced meshes.

12. The fusion device according to claim 1, wherein said side wall of said hollow container body has a structure selected from the group consisting of:
a spiral-shaped structure;
a fibrous structure; and
a composite structure.

13. The device according to claim 12, wherein said granular osteosynthesis material is in the form of tablets comprising an amount of cortical bone material and an amount of trabecular bone material in a prefixed proportion.

14. The device according to claim 1, wherein said fusion device is in an axially precompressed configuration from a rest position to a precompressed position and, and wherein a wrapper is provided to keep said fusion device at said precompressed position.

15. The fusion device according to claim 1, wherein said granular osteosynthesis material is human or animal bone material.

16. The fusion device according to claim 1, wherein said osteosynthesis material comprises bone growth factors.

17. A vertebral fusion system comprising:
a plurality of devices according to claim 1,
wherein said plurality of devices is selected from the group consisting of:
said fusion device configured for insertion between two mutually facing joint surfaces of said two vertebral bodies;
said fusion device configured for insertion into said interspinous space;
said interarticular fusion device configured for insertion between said cooperating articular facets;
said fusion device configured for insertion between said corresponding transverse processes, wherein said vertebral fusion device comprises a couple of fusion devices for insertion between respective couples of right and left transverse processes.

18. The fusion system according to claim 17, comprising said fusion device configured for insertion into said interspinous space, at least one fusion device configured for insertion between said two joint surfaces and a couple of fusion devices configured for insertion between respective couples of cooperating articular facets.

19. The fusion system according to claim 17, comprising a plurality of fusion devices configured for insertion between said two joint surfaces, comprising a front device and a rear device configured for being placed at front and rear positions, respectively, within said intervertebral space, wherein said front device has a height H''' higher than a height H'' of said rear device, in order to prevent said adjacent vertebrae from becoming kyphotic.

20. The fusion device according to claim 1, wherein the fusion device has a height set between 6 mm and 18 mm.

* * * * *